US010376605B1

(12) United States Patent
Majdali et al.

(10) Patent No.: US 10,376,605 B1
(45) Date of Patent: Aug. 13, 2019

(54) SYSTEMS AND METHODS FOR SANITIZING AMUSEMENT PARK ARTICLES (71) Applicant: Universal City Studios LLC, Universal City, CA (US)

(72) Inventors: David Majdali, Orlando, FL (US); John Ugrin, Orlando, FL (US)

(73) Assignee: Universal City Studios LLC, Universal City, CA (US)

( * ) Notice: Subject to any disclaimer, the term of this patent is extended or adjusted under 35 U.S.C. 154(b) by 0 days.

(21) Appl. No.: 15/937,609

(22) Filed: Mar. 27, 2018

(51) Int. Cl.
*A61L 2/10* (2006.01)
*A63G 31/00* (2006.01)
*A61L 2/08* (2006.01)
*A61L 2/26* (2006.01)

(52) U.S. Cl.
CPC ............... *A61L 2/10* (2013.01); *A61L 2/088* (2013.01); *A61L 2/26* (2013.01); *A63G 31/00* (2013.01); *A61L 2202/11* (2013.01); *A61L 2202/121* (2013.01); *A61L 2202/14* (2013.01); *A61L 2202/15* (2013.01); *A61L 2202/16* (2013.01); *A61L 2202/17* (2013.01)

(58) Field of Classification Search
CPC ... A61L 2/10; A61L 2/088; A61L 2/26; A61L 2202/11; A61L 2202/121; A61L 2202/14; A61L 2202/15; A61L 2202/16; A61L 2202/17; A63G 31/00
USPC ... 250/453.11, 454.11, 455.11, 493.1, 494.1, 250/504 R
See application file for complete search history.

(56) References Cited

U.S. PATENT DOCUMENTS

| | | | |
|---|---|---|---|
| 6,039,928 | A | 3/2000 | Roberts |
| 7,160,566 | B2 | 1/2007 | Fink et al. |
| 7,791,044 | B1 | 9/2010 | Taylor et al. |
| 9,050,383 | B2 | 6/2015 | Gray |
| 9,144,618 | B2 | 9/2015 | Kreitenberg |
| 2002/0085947 | A1 | 7/2002 | Deal |

(Continued)

FOREIGN PATENT DOCUMENTS

| | | |
|---|---|---|
| CH | 293571 A | 9/1953 |
| CN | 2080843 | 7/1991 |

(Continued)

OTHER PUBLICATIONS

The Hepacart Blog, Information on Specialized Infection Control, Dust Containment Products, and Facility Management, What is Far-UV Sterilray⁴?, Jun. 20, 2017, pp. 1-7, http://www.hepacart.com/blog/what-is-far-uv-sterilray.

(Continued)

*Primary Examiner* — Nicole M Ippolito
(74) *Attorney, Agent, or Firm* — Fletcher Yoder, P.C.

(57) ABSTRACT

A sanitization system for an amusement park includes a compartment disposed in a ride vehicle of an amusement park ride, where the compartment is configured to receive an article of the amusement park ride, an ultraviolet light source disposed in the compartment, where the ultraviolet light source is configured to transmit ultraviolet light toward a surface of the article when the article is positioned in the compartment, and a nozzle disposed in the compartment, wherein the nozzle is configured to direct a sanitizing fluid toward the surface of the article when the article is positioned in the compartment.

20 Claims, 8 Drawing Sheets

(56) References Cited

U.S. PATENT DOCUMENTS

| | | |
|---|---|---|
| 2003/0150475 A1 | 8/2003 | Abrams et al. |
| 2005/0022844 A1 | 2/2005 | Field et al. |
| 2007/0012340 A1* | 1/2007 | Jones ............... A61L 2/10 134/45 |
| 2007/0057197 A1 | 3/2007 | Chor |
| 2007/0164232 A1 | 7/2007 | Rolleri et al. |
| 2007/0258851 A1 | 11/2007 | Fogg et al. |
| 2008/0118395 A1 | 5/2008 | Benedek |
| 2008/0178412 A1* | 7/2008 | Kiter ............... A61L 2/10 15/309.2 |
| 2008/0199354 A1 | 8/2008 | Gordon |
| 2008/0289649 A1 | 11/2008 | Woytkiw |
| 2009/0050174 A1* | 2/2009 | Gheparde ............... B08B 3/00 134/1 |
| 2009/0304553 A1 | 12/2009 | Gordon |
| 2009/0311149 A1 | 12/2009 | Freedgood |
| 2010/0266446 A1 | 10/2010 | Constantacos |
| 2011/0168898 A1 | 7/2011 | Statham et al. |
| 2011/0243789 A1 | 10/2011 | Roberts |
| 2011/0293484 A1 | 12/2011 | Stausgaard et al. |
| 2012/0273340 A1 | 11/2012 | Felix |
| 2014/0030161 A1 | 1/2014 | Alovisi |
| 2014/0096801 A1 | 4/2014 | McCormick et al. |
| 2014/0158910 A1 | 6/2014 | Fletcher |
| 2015/0190537 A1 | 7/2015 | Kerr |
| 2015/0190538 A1* | 7/2015 | Olvera ............... A61L 2/22 422/107 |
| 2015/0209459 A1 | 7/2015 | Kreitenberg |
| 2015/0290346 A1 | 10/2015 | Kassel et al. |
| 2016/0220716 A1 | 8/2016 | Childress et al. |
| 2016/0346704 A1 | 12/2016 | Wagner |
| 2017/0000915 A1 | 1/2017 | Cottone |
| 2017/0043044 A1 | 2/2017 | Sobhy |
| 2018/0280554 A1 | 10/2018 | Khajavi et al. |

FOREIGN PATENT DOCUMENTS

| | | |
|---|---|---|
| DE | 4205113 C1 | 4/1993 |
| DE | 102009040765 A1 | 2/2011 |
| EP | 0772226 A2 | 5/1997 |
| FR | 2129901 A1 | 11/1972 |
| KR | 101408941 B1 | 6/2014 |
| KR | 20150017544 A | 2/2015 |
| WO | 2010060079 A1 | 5/2010 |

OTHER PUBLICATIONS

Columbia University Medical Center Newsroom, Narrow Wavelength of UV Light Safely Kills Drug-Resistant Bacteria, Jun. 8, 2016, pp. 1-5, http://newsroom.cumc.columbia.edu/blog/2016/06/08/narrow-wavelength-uv-light-safely-kills-drug-resistant-bacteria-2/.

Cohen, Jon, Could ultraviolet lamps slow the spread of flu?, Science Magazine, Jan. 3, 2018, pp. 1-4, http://www.sciencemag.org/news/2018/01/could-ultraviolet-lamps-slow-spread-flu?utm_source=newsfromscience&utm_medium=facebook-text&utm_campaign=flulamp-17172.

PCT/US2018/061329 Search Report and Written Opinion dated Feb. 5, 2019.

* cited by examiner

SYSTEMS AND METHODS FOR SANITIZING AMUSEMENT PARK ARTICLES

BACKGROUND

The present disclosure relates generally to the field of amusement parks. More specifically, embodiments of the present disclosure relate to a sanitization system for an amusement park.

This section is intended to introduce the reader to various aspects of art that may be related to various aspects of the present disclosure, which are described below. This discussion is believed to be helpful in providing the reader with background information to facilitate a better understanding of the various aspects of the present disclosure. Accordingly, it should be understood that these statements are to be read in this light, and not as admissions of prior art.

Amusement parks contain a variety of rides and other features that provide unique experiences to each park guest. In some cases, ride cars, handles, interactive components, or other features and/or articles that guests contact may accumulate bacteria or other undesirable substances. Accordingly, amusement parks may include processes for removing such substances from surfaces that guests frequently contact. It is now recognized that existing cleaning processes are time consuming, and thus, may increase wait times for guests to experience the ride or attraction. Additionally, it is now recognized that existing cleaning processes may be performed inefficiently, such as by removing an amusement park article from a ride vehicle, cleaning the article, and returning the article to the ride vehicle.

SUMMARY

Certain embodiments commensurate in scope with the originally claimed subject matter are summarized below. These embodiments are not intended to limit the scope of the disclosure, but rather these embodiments are intended only to provide a brief summary of certain disclosed embodiments. Indeed, the present disclosure may encompass a variety of forms that may be similar to or different from the embodiments set forth below.

In one embodiment, a sanitization system for an amusement park includes a compartment disposed in a ride vehicle of an amusement park ride, wherein the compartment is configured to receive an article of the amusement park ride, an ultraviolet light source disposed in the compartment, wherein the ultraviolet light source is configured to transmit ultraviolet light toward a surface of the article when the article is positioned in the compartment, and a nozzle disposed in the compartment, wherein the nozzle is configured to direct a sanitizing fluid toward the surface of the article when the article is positioned in the compartment.

In another embodiment, a system includes an amusement park ride and a sanitization system. The amusement park ride includes a ride path and a ride vehicle, wherein the ride vehicle is configured to transport a guest along the ride path in a direction of the amusement park ride. The sanitization system is disposed within the ride vehicle, and the sanitization system includes a compartment configured to receive an article of the amusement park ride, an ultraviolet light source disposed in the compartment, wherein the ultraviolet light is configured to transmit ultraviolet light toward a surface of the article when the article is positioned in the compartment, and a nozzle disposed in the compartment, wherein the nozzle is configured to direct a sanitizing fluid toward the surface of the article when the article is positioned in the compartment.

In another embodiment, a system includes a sanitization system of an amusement park, wherein the sanitization system is disposed within a ride vehicle of an amusement park ride, and wherein the sanitization system includes a compartment configured to receive an article of the amusement park ride, an ultraviolet light source disposed in the compartment, wherein the ultraviolet light is configured to transmit ultraviolet light toward a surface of the article when the article is positioned in the compartment, and an article rotation device at least partially disposed in the compartment, wherein the article rotation device includes a plurality of receptacles, and wherein each receptacle of the plurality of receptacles is configured to receive a corresponding article of the amusement park ride.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

One or more specific embodiments of the present disclosure will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Amusement parks feature a wide variety of entertainment, such as amusement park rides, performance shows, and games. As used herein, amusement park rides may include roller coasters, dark rides, theme rides, tower rides, water rides, among others. The different types of entertainment may include features and/or articles that enhance a guest's experience at the amusement park. In some instances, amusement park rides, games, interactive equipment, and/or other articles include surfaces (e.g., handles, knobs, handheld or wearable articles, goggles or glasses) that guests frequently contact or touch. Such surfaces may accumulate bacteria and/or other undesirable substances as guests contact the surfaces and/or as the surfaces come into contact with air, water, mist, and/or spilled solids or liquids in an environment of the ride or article. As such, amusement parks may have protocol in place for periodic sanitization of the surfaces to remove the bacteria or other undesirable substances. For example, amusement parks may remove various articles (e.g., handheld devices consistent with a theme of a ride, wearable devices worn by guests during a ride, glasses or goggles worn by guests during a ride, interactive devices used by guests during the ride) from a ride vehicle and utilize sanitization spray (e.g., soap or anti-bacterial liquid) to clean the surfaces which may be exposed to bacteria and other undesirable substances during routine maintenance of the amusement park ride and/or during off-hours of the amusement park (e.g., when the amusement park is closed).

In some cases, articles of an amusement park ride may be relatively expensive, such that the amusement park purchases a finite amount of the articles to make available for guests. Employees of the amusement park may remove such articles from a ride vehicle to clean the articles between adjacent uses by guests of the amusement park to remove any bacteria and/or other undesirable substances from the articles. It is now recognized that removing articles from a ride vehicle and cleaning the articles using traditional sanitization methods is time consuming, thereby reducing an amount of guests that may experience the amusement park ride, game, interactive feature, and/or entertainment show throughout a given day.

Embodiments of the present disclosure are directed to an enhanced sanitization system for articles that may be included on a ride vehicle of an amusement park ride that utilizes sanitization spray, or ultraviolet light, or both to periodically remove bacteria and other undesirable substances from the articles of the ride vehicle that are frequently contacted by guests. In some embodiments, the articles of the amusement park ride may be placed into a compartment of the ride vehicle by a particular guest at the conclusion of the amusement park ride (e.g., when the ride vehicle reaches an unloading region where guests exit the ride vehicle). The compartment may include ultraviolet light sources, spray nozzles, and/or dryers to sanitize the article of the amusement park ride as the ride vehicle is transported from the unloading region to a loading region (e.g., a portion of a ride path of the ride vehicle where guests enter the ride vehicle). As such, a guest entering the ride vehicle at the loading region may then utilize the sanitized article of the amusement park ride throughout the duration of the amusement park ride (e.g., as the ride vehicle travels along the ride path from the loading region to the unloading region).

In other embodiments, the ride vehicle may include multiple compartments, which may enable a first article of the amusement park ride to undergo sanitization throughout the duration of the ride, while a second article of the amusement park ride is utilized by a guest riding in the ride vehicle. For instance, a first compartment may house the first article of the amusement park ride and perform sanitization on the first article of the amusement park ride. Additionally, a second compartment may be empty throughout the duration of the ride and then open to prompt the guest to return the second amusement park article to the second compartment when the ride vehicle reaches the unloading region. Accordingly, a subsequent guest that rides the ride vehicle may utilize the first article of the amusement park ride, while the second article of the amusement park ride undergoes sanitization. In still further embodiments, the compartment may include an article rotation device, which may include a plurality of rotating, moving, or otherwise actuated receptacles, where each receptacle is configured to receive an article of the amusement park ride. The actuated receptacles may alternate sanitization cycles for corresponding articles disposed in the receptacles within a single compartment of the ride vehicle.

In an embodiment, the sanitization system is configured to at least partially remove bacteria and other undesirable substances from surfaces of the articles of the amusement park ride on-board the ride vehicle. As such, the frequency and efficiency of sanitization of the amusement park ride increases, which may enhance the experience of guests visiting the amusement park.

Figure 1:
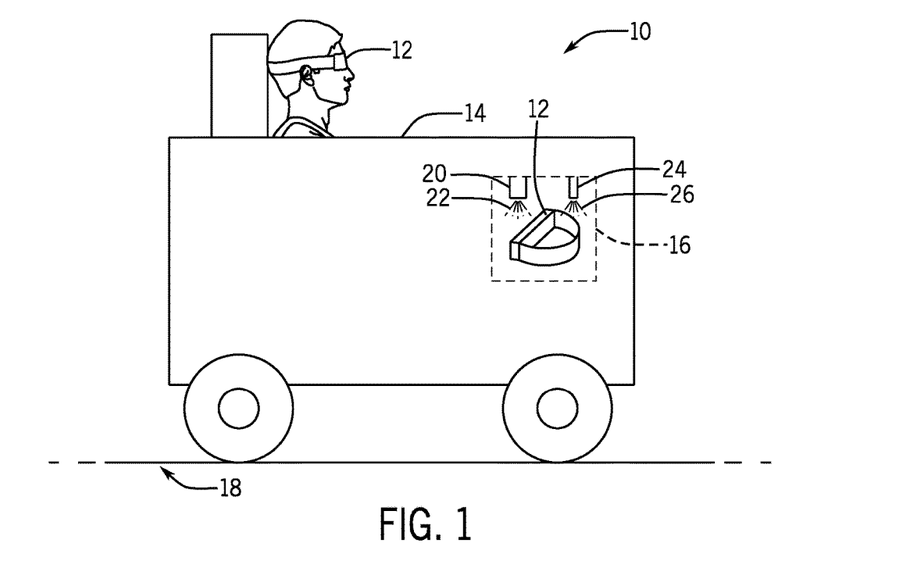
FIG. 1 illustrates an embodiment of a sanitization system for an amusement park article, in accordance with an aspect of the present disclosure.

Turning to the figures, FIG. 1 illustrates an embodiment of a sanitization system 10 for cleaning an article 12 of an amusement park ride on a ride vehicle 14. As shown in the illustrated embodiment of FIG. 1, the sanitization system 10 may include a compartment 16 that is included within the ride vehicle 14 for sanitizing the article 12. In some embodiments, the article 12 includes a pair of glasses or goggles (e.g., glasses used for viewing a 3-dimensional video, clip, or effects, virtual reality goggles, augmented reality goggles) worn by a guest experiencing the amusement park ride. In other embodiments, the article 12 may include an interactive component of the amusement park (e.g., a handheld component configured to communicate with structures or actuated devices of the amusement park ride), a wearable device associated with a guest profile of the guest, or another suitable component that is held or otherwise contacted by guests of the amusement park ride. While the illustrated embodiments of the present disclosure show the article 12 as a pair of glasses or goggles, it should be understood that the article 12 may include any suitable component that is frequently contacted by guests of the amusement park.

The compartment is configured to receive the article 12 and sanitize the article 12 as the ride vehicle 14 travels along a ride path 18. The compartment 16 may include an ultraviolet light source 20 configured to emit ultraviolet light 22 toward the article 12 to remove bacteria and other undesirable substances from surfaces of the article 12 that the guests frequently contact. The ultraviolet light 22 contacts the surfaces of the article 12 and removes the bacteria and other undesirable substances (e.g., viruses) that may be present on the surfaces. In some embodiments, the compartment 16 also includes a nozzle 24, which is configured to spray the article 12 with a sanitizing mist or liquid 26 (e.g., cleaning solution). For instance, the nozzle 24 receives a fluid (e.g., the cleaning solution) from a fluid source and sprays the sanitizing mist or liquid 26 toward the article 12 before, after, or simultaneously with the ultraviolet light 22. As such, the sanitizing mist or liquid 26 may further sanitize the article 12 in conjunction with the ultraviolet light 22. In some embodiments, the nozzle 24 may also represent a dryer that operates to dry the sanitizing mist or liquid 26 subsequent to emission from the nozzle 24.

In some embodiments, the ultraviolet light source 20 and/or the nozzle 24 are activated when the ride vehicle 14 is traveling between a guest unloading region and a guest loading region (e.g., when the ride vehicle 14 includes a single compartment 16). As such, a speed of the ride vehicle 14 may be slowed or reduced to provide the article 12 with sufficient exposure to the ultraviolet light source 20 for cleaning of the article 12. As a non-limiting example, movement of the ride vehicle 14 may be reduced to ensure that the article 12 is exposed to the ultraviolet light source 20 for a duration of between 1 second and 5 minutes, between 5 seconds and 45 seconds, or between 10 seconds and 20 seconds, or any other suitable duration. In other embodiments, the ultraviolet light source 20 and/or the nozzle 24 are activated when the ride vehicle 14 is traveling between the guest loading region and the guest unloading region (e.g., when the ride vehicle 14 includes multiple compartments 16 and/or an article rotation device for a single compartment 16). In still further embodiments, the ultraviolet light source 20 and/or the nozzle 24 are activated when the ride vehicle 14 is traveling along substantially the entire ride path 18 (e.g., when the compartment 16 is in a closed position). Accordingly, sanitization of the article 12 is systematically performed during operating hours of the amusement park ride (e.g., when guests are riding the amusement park ride on other ride vehicles). Additionally, sanitization of the article 12 may be performed during off-hours of the amusement park ride (e.g., when guests are not positioned within the ride vehicles 14 of the amusement park ride).

The ultraviolet light source 20 emits the ultraviolet light 22, which cleans the surfaces of the article 12. In some embodiments, the ultraviolet light 22 may include a predetermined wavelength suitable for removing common bacteria and/or other undesirable substances present on the surfaces of the article 12. The wavelength of the ultraviolet light 22 may be between 122 and 200 nanometers, thereby emitting far ultraviolet ("FUV") light to clean the surfaces of the article 12. FUV may be beneficial for killing common bacteria or undesirable substances on the surfaces of the article 12. In other embodiments, the ultraviolet light 22 may include any suitable wavelength (e.g., between 10 and 400 nanometers).

Figure 2:
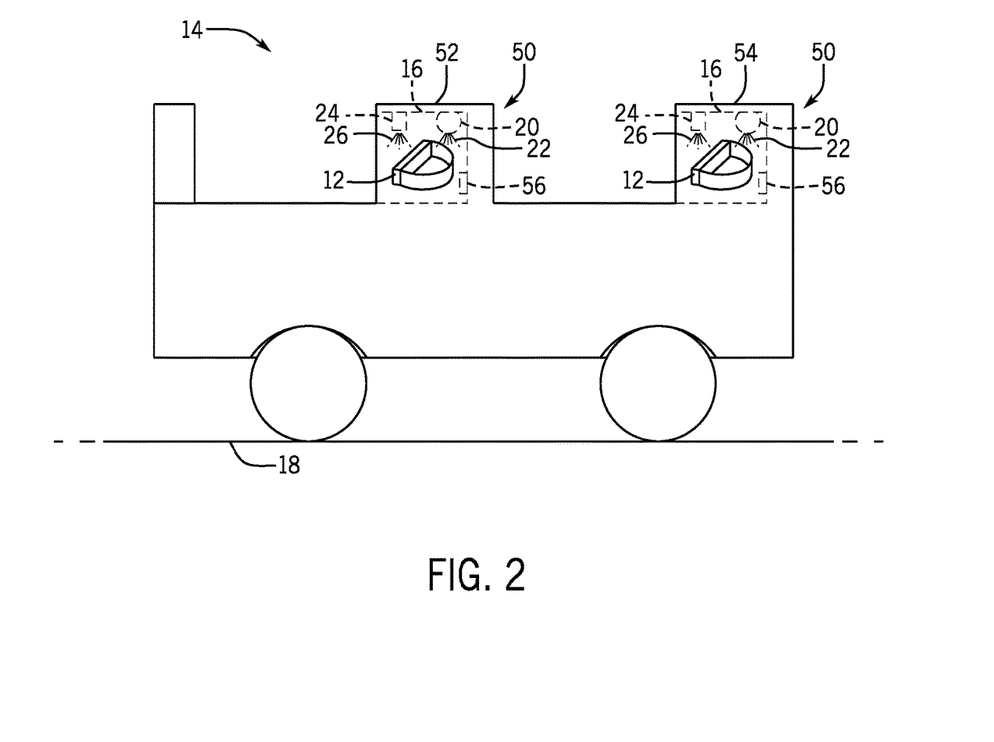
FIG. 2 illustrates an elevation view of an embodiment of a ride vehicle having the sanitization system of FIG. 1, in accordance with an aspect of the present disclosure.

FIG. 2 illustrates an elevation view of the ride vehicle 14 having two of the compartments 16, which are configured to receive and ultimately sanitize one or more of the articles 12. As shown in the illustrated embodiment of FIG. 2, the compartments 16 are disposed within portions 50 of the ride vehicle 14. For instance, the compartments 16 may be positioned in a seatback 52 of the ride vehicle 14 and/or in a body 54 of the ride vehicle 14 (e.g., when a seatback 52 is not available, such as for a front seat of the ride vehicle 14). Accordingly, the compartments 16 are configured to sanitize the articles 12 of the amusement park ride on board the ride vehicle 14, such that the articles 12 are not removed from the ride vehicle 14, thereby reducing an amount of time to complete sanitization of the articles 12. Further, performing sanitization of the articles 12 on the ride vehicle may reduce a number of the articles 12 that the amusement park purchases and/or has available because the increased speed of the sanitization process enables clean articles 12 to be available to guests more frequently. Further still, the articles 12 on the ride vehicle may not be transported to a cleaning facility remote from the amusement park ride. As such, costs associated with transferring the articles 12 to the remote cleaning facility are reduced and/or eliminated. Additionally, a risk of damaging the articles 12 during transportation to the remote cleaning facility are also reduced.

As shown in the illustrated embodiment of FIG. 2, the compartments 16 may each include the ultraviolet light source 20 and the nozzle 24. In some embodiments, the nozzle 24 is configured to direct the sanitizing mist or liquid 26 toward a respective article 12 before the ultraviolet light source 20 transmits the ultraviolet light 22 toward the article 12. As such, the ultraviolet light source 20 may act to dry the article 12 and/or remove residual sanitizing mist or liquid 26 that may be present on or within the article 12. Additionally or alternatively, the compartments 16 may include a fan, dryer, or heater 56 that further removes residual sanitizing mist or liquid 26 from the article 12. In other embodiments, the nozzle 24 may direct the sanitizing mist or liquid 26 toward the article 12 after the ultraviolet light source 20 transmits the ultraviolet light 22 toward the article 12. In still further embodiments, the nozzle 24 directs the sanitizing mist or liquid 26 toward the article 12 and the ultraviolet light source 20 transmits the ultraviolet light 22 toward the article 12 substantially simultaneously.

Figure 3:
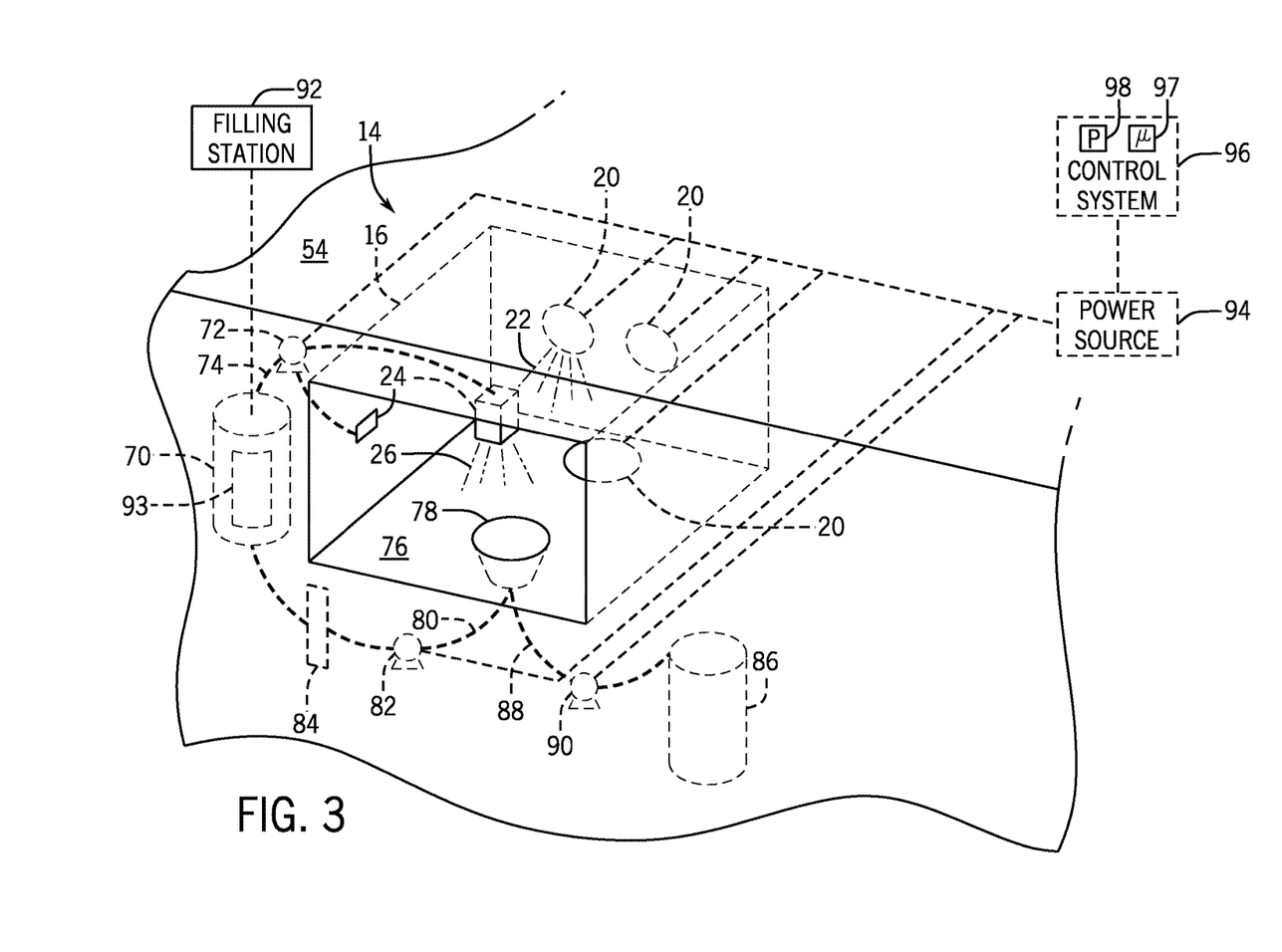
FIG. 3 illustrates a perspective view of an embodiment of a compartment of the sanitization system of FIGS. 1 and 2, in accordance with an aspect of the present disclosure.

FIG. 3 illustrates a perspective view of the compartment 16 within the ride vehicle 14. As shown in the illustrated embodiment of FIG. 3, the compartment includes one or more of the ultraviolet light sources 20 and one or more of the nozzles 24. In some embodiments, the one or more nozzles 24 are fluidly coupled to a storage tank 70 that receives and stores the sanitizing mist or liquid 26. For instance, a pump 72 is disposed along a conduit 74 (e.g., a pipe or tubing) that fluidly couples the storage tank 70 to the one or more nozzles 24. The pump 72 may draw the sanitizing mist or liquid 26 from the storage tank 70 and flow the sanitizing mist or liquid 26 toward the one or more nozzles 24. In some embodiments, the pump 72 directs the sanitizing mist or liquid 26 toward each nozzle 24 of the one or more nozzles 24 included in the compartment 16. In other embodiments, each nozzle 24 of the one or more nozzles 24 includes a corresponding pump 72 that draws the sanitizing mist or liquid 26 from the storage tank 70.

The storage tank 70 may be disposed within the ride vehicle 14 (e.g., the body 54 of the ride vehicle 14), such that the storage tank 70 is hidden from the guests experiencing the amusement park ride. Additionally or alternatively, the storage tank 70 may be utilized to supply the sanitizing mist or liquid 26 to multiple compartments 16 included in the ride vehicle 14. For example, the ride vehicle 14 may include a compartment 16 for each seat of the ride vehicle 14. Accordingly, the storage tank 70 may be configured to supply the sanitizing mist or liquid 26 to any number of the compartments 16 included in the ride vehicle 14. In other embodiments, each compartment 16 included within the ride vehicle 14 has a corresponding storage tank 70 for supplying the sanitizing mist or liquid 26.

In any case, when the sanitizing mist or liquid 26 is sprayed from the one or more nozzles 24 toward the article 12, the sanitizing mist or liquid 26 may collect within a bottom 76 of the compartment 16. Accordingly, the compartment 16 may include a drain 78 for collecting the residual sanitizing mist or liquid 26. In some embodiments, the drain 78 is fluidly coupled to the storage tank 70 via a conduit 80 (e.g., a pipe or tubing). A pump 82 (e.g., a second pump) directs the residual sanitizing mist or liquid 26 from the drain 78 toward the storage tank 70, such that the residual sanitizing mist or liquid 26 is recycled (e.g., used for multiple sanitization processes for cleaning the articles 12). To remove any particulates and/or undesirable substances collected by the sanitizing mist or liquid 26, a filter 84 (e.g., a mesh screen, a sieve, an adsorbent filter, an absorbent filter) may be disposed along the conduit 80 between the drain 78 and the storage tank 70. The filter 84 may then remove any undesirable substances from the sanitizing mist or liquid 26 before the sanitizing mist or liquid 26 is directed back to the one or more nozzles 24.

In other embodiments, the sanitizing mist or liquid 26 may not be recycled or reused for subsequent sanitization processes. Instead, the sanitizing mist or liquid 26 is directed to a waste container 86, which is fluidly coupled to the drain 78 via a conduit 88 (e.g., a pipe or tubing). A pump 90 (e.g., the second pump 82 or another pump) may be disposed along the conduit 88 to direct the sanitizing mist or liquid 26 toward the waste container 86. In other embodiments, the sanitizing mist or liquid 26 flows from the drain 78 to the waste container 86 via gravitational forces due to the arrangement of components (e.g., the waste container 86) with respect to the compartment 16. Similar to the storage tank 70, the waste container 86 may be disposed in the ride vehicle 14, such that the waste container 86 is hidden from the guests. Additionally, the waste container 86 may receive the sanitizing mist or liquid 26 from multiple compartments 16 of the ride vehicle 14. In other embodiments, the waste container 86 receives the sanitizing mist or liquid 26 from a single compartment 16.

In certain embodiments, the storage tank 70 may be replenished periodically as the sanitizing mist or liquid 26 is utilized, evaporates, and/or otherwise is not recycled back to the storage tank 70. As such, the amusement park ride may include a filling station 92 that may replenish the sanitizing mist or liquid 26 in the storage tank 70. For instance, the filling station 92 may be positioned either at the unloading region of the ride path 18 and/or between the unloading region and the loading region of the ride path 18 (e.g., with respect to a direction of travel of the ride vehicle 14). The filling station 92 is configured to fluidly couple a source of the sanitizing mist or liquid 26 to the storage tank 70 and direct fresh sanitizing mist or liquid 26 into the storage tank 70. The source of the sanitizing mist or liquid 26 may be coupled to the storage tank 70 manually (e.g., by an operator of the amusement park ride) and/or automatically (e.g., via actuated members that move along the ride path 18 with the ride vehicle 14). In other embodiments, the storage tank 70 may be refilled (e.g., manually or automatically) as part of routine maintenance of the ride vehicle 14, during off-hours of the amusement park ride (e.g., when guests are not experiencing the amusement park ride), and/or during other suitable times.

Further still, the storage tank 70 may include a heating element 93 configured to transfer thermal energy (e.g., heat) to the sanitizing mist or liquid 26 stored in the storage tank 70. Accordingly, warm sanitizing mist or liquid 26 may be directed toward surfaces of the article 12 via the nozzles 24. Heating the sanitizing mist or liquid 26 may enhance the sanitization process of the article 12 because warm fluid may be more effective at removing solids and/or killing bacteria present on the surfaces of the article 12. For instance, increasing a temperature of the sanitizing mist or liquid 26 may breakdown a greater amount of solidified material present on the surface when compared to a lower-temperature sanitizing mist or liquid 26. Additionally, bacteria may not be able to survive in high-temperature environments. Therefore, increasing the temperature of the sanitizing mist or liquid 26 may effectively kill more bacteria when compared to a lower-temperature sanitizing mist or liquid 26.

As shown in the illustrated embodiment of FIG. 3, the one or more ultraviolet light sources 20 and the pumps 72, 82, and/or 90 are coupled to a power source 94. The power source 94 may be a single power source 94 that is utilized to power multiple compartments 16 and/or other components (e.g., lights, actuated members, sounds, displays) of the ride vehicle 14. In other embodiments, the power source 94 is configured to supply power to components for a single compartment 16. The power source 94 may include a battery, a generator, and/or another suitable power source. In any case, the power source 94 may be controlled by a control system 96. In some embodiments, the control system 96 is configured to selectively operate the one or more ultraviolet light sources 20 and the pumps 72, 82, and/or 90 via the power source 94. Accordingly, the sanitizing mist or liquid 26 may be sprayed toward the article 12, while the one or more ultraviolet light sources 20 are deactivated (e.g., not transmitting the ultraviolet light 22), or vice versa. In other embodiments, the control system 96 is communicatively coupled to one or more actuators configured to adjust a position of valves disposed along the conduits 74, 80, and/or 88. In such embodiments, the control system 96 may control a flow of the sanitizing spray or mist 26 via the positions of such valves.

In any case, the control system 96 may include instructions stored on machine-readable medium 97 (e.g., memory) and executable by a processor 98. The instructions are configured to activate and/or deactivate the one or more ultraviolet light sources 20 and/or the pumps 72, 82, and/or 90. In some embodiments, the control system 96 is configured to receive feedback indicative of a position of the ride vehicle 14 and/or indicative of a position of a door 100 for the compartment 16 (see, e.g., FIG. 5). As such, the control system 96 may activate and/or deactivate the one or more ultraviolet light sources 20 and/or the pumps 72, 82, 90 when the ride vehicle 14 reaches a predetermined position along the ride path 18 and/or when the door 100 of the compartment 16 is determined to be in an open position or a closed position. As such, the sanitization process may be activated when the compartment 16 is sealed (e.g., the door 100 is in the closed position) and the control system 96 determines that the ride vehicle 14 is in a position where the articles 12 are disposed within the compartment 16.

Figure 4:
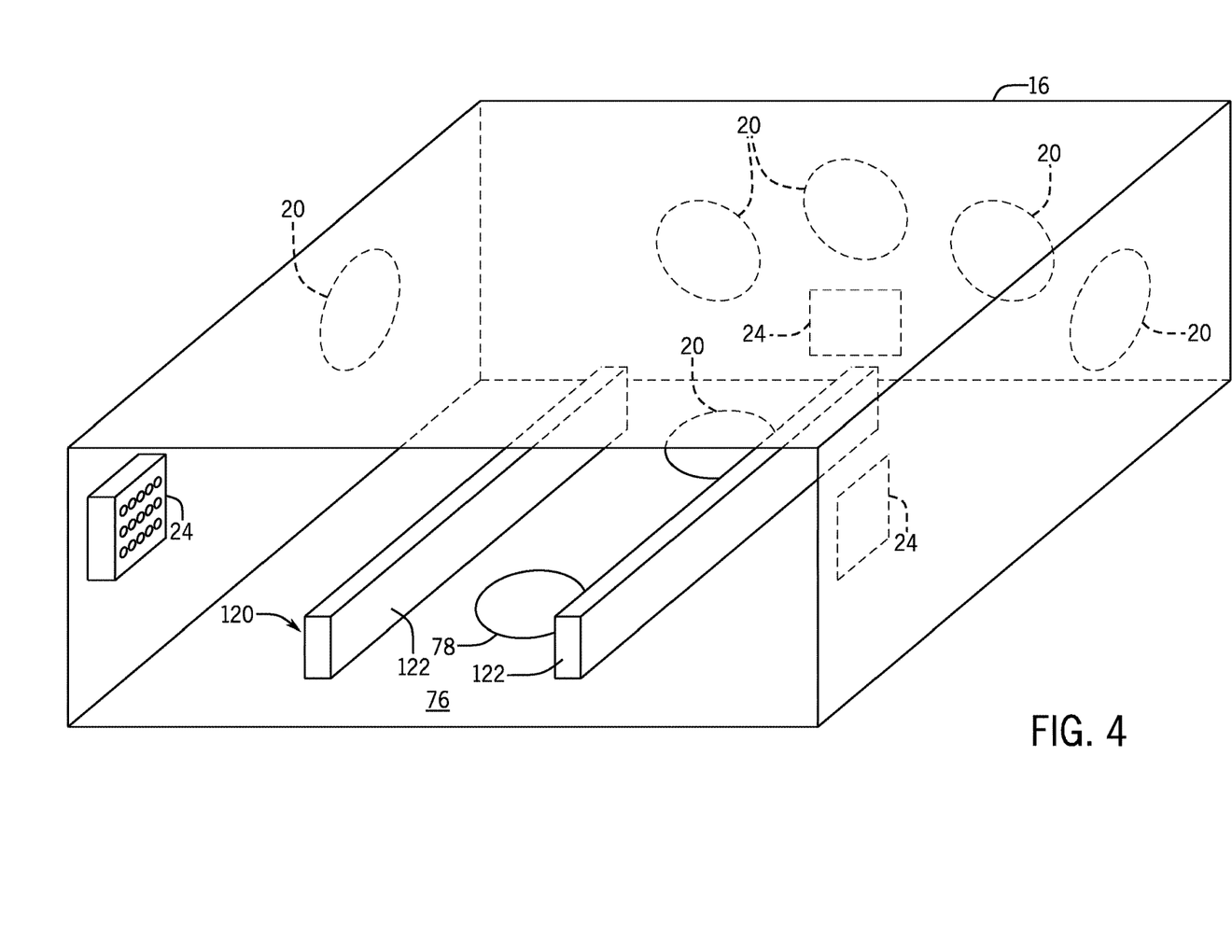
FIG. 4 illustrates a perspective view of an embodiment of the compartment of the sanitization system of FIG. 3 having a rack for receiving the amusement park article, in accordance with an aspect of the present disclosure.

FIG. 4 illustrates a perspective view of the compartment 16 having a rack 120 that is configured to situate the article 12 within the compartment 16 in a position that exposes predetermined surfaces of the article 12 (e.g., surfaces frequently contacted by guests of the amusement park ride) to the ultraviolet light 22 as well as the sanitizing mist or liquid 26. As shown in the illustrated embodiment of FIG. 4, the rack 120 may include a pair of protrusions 122 that extend along the bottom 76 of the compartment 16. In other embodiments, the rack 120 may include another structural component disposed within the compartment that complements or accommodates a shape of the article 12 and situates the article 12 in a position that enhances exposure of the predetermined surfaces of the article 12 to the ultraviolet light 22 and/or the sanitizing mist or liquid 26. For instance, the rack 120 may include a conical stand configured to receive and hold the article 12, a wire rack configured to receive and hold the article 12, a perforated shelf configured to receive and hold the article 12, or a combination thereof. In addition to positioning the article 12 to enhance exposure of the predetermined surfaces to the ultraviolet light 22 and/or the sanitizing mist or liquid 26, the rack 120 also enables the article 12 to be offset from the bottom 76 of the compartment 16. Thus, the residual sanitizing mist or liquid 26 may not collect on a surface of, or within, the article 12 but drip down onto the bottom surface 76 toward the drain 78.

As discussed above, in some embodiments, the ride vehicle 14 includes a single compartment 16 for a corresponding article 12. In such embodiments, a guest may place the article 12 into the compartment 16 upon completion of the amusement park ride (e.g., when the ride vehicle 14 reaches an unloading region along the ride path 18). The ride vehicle 14 may then travel along the ride path 18 from the unloading region to a loading region while the article 12 is sanitized within the compartment 16. As such, a guest entering the ride vehicle 14 at the loading region may then remove the clean article 12 from the compartment 16 for use throughout the duration of the amusement park ride (e.g., as the ride vehicle 14 travels along the ride path 18 from the loading region to the unloading region). In other embodiments, the ride vehicle 14 includes multiple compartments 16 (e.g., a carousel of compartments 16 that rotate relative to an access point), where each compartment 16 is configured to receive and sanitize a respective article 12. In still further embodiments, a single compartment 16 is configured to receive and/or sanitize multiple articles 12.

Figure 5:
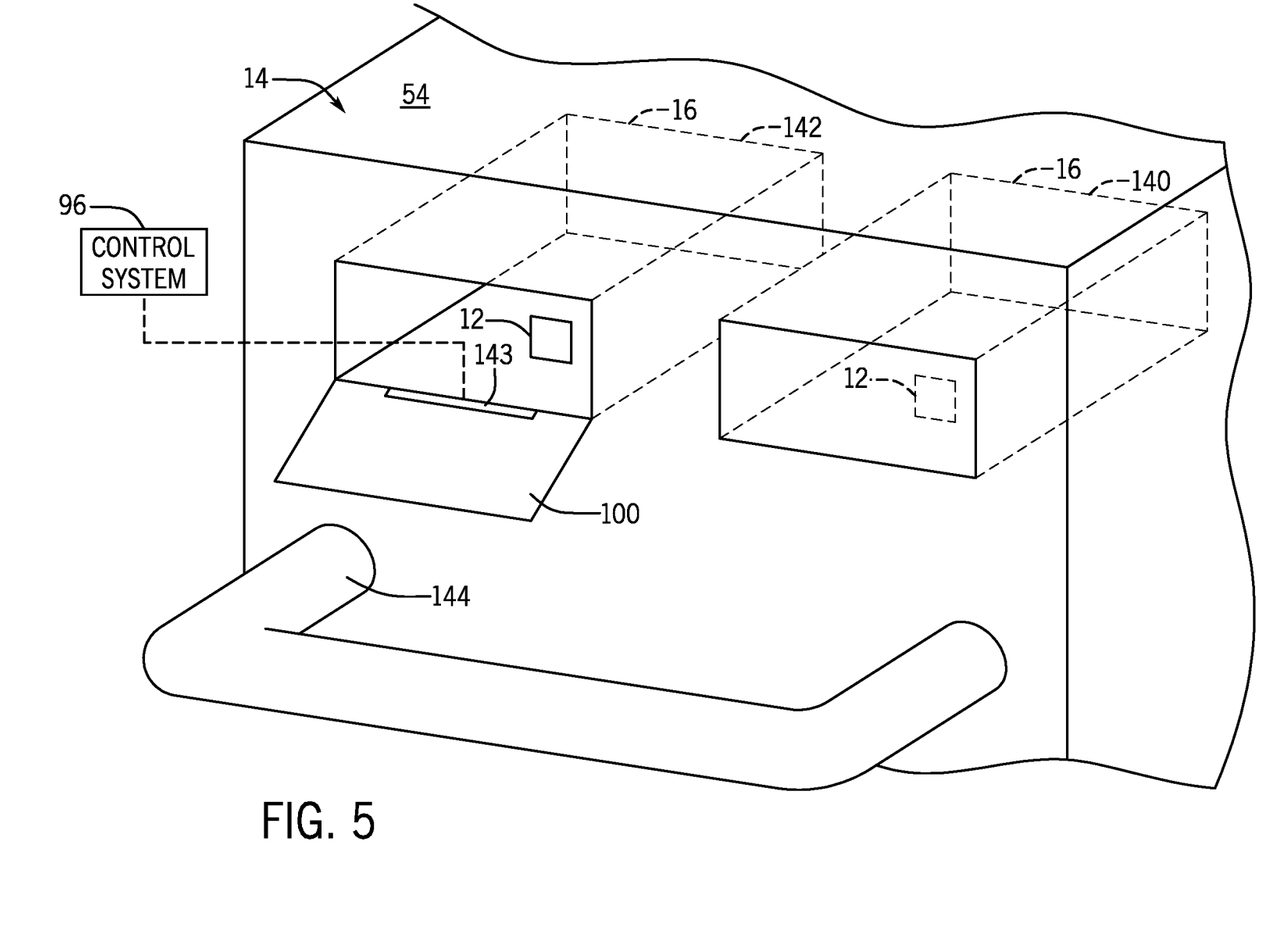
FIG. 5 illustrates a partial perspective view of an embodiment of the ride vehicle having two compartments of the sanitization system, in accordance with an aspect of the present disclosure.

For example, FIG. 5 is an embodiment of a partial view of the ride vehicle 14 having adjacent compartments 16 for a single seat of the ride vehicle 14. As such, a guest positioned in the ride vehicle 14 may utilize a first article 12 throughout the duration of the amusement park ride (e.g., as the ride vehicle 14 travels from the loading region to the unloading region along the ride path 18). Further, a second article 12 may be sanitized in a first compartment 140 throughout the duration of the amusement park ride while the guest utilizes the first article 12. At the conclusion of the amusement park ride (e.g., when the ride vehicle 14 reaches the unloading region), the door 100 of a second compartment 142 may open (e.g., the control system 96 controls an actuator 143, such as a motor, that opens and closes the door 100). Accordingly, the guest may place the first article 12 into the second compartment 142 for sanitization. The door 100 of the second compartment 142 may then close (e.g., the control system 96 controls the actuator 143 that opens and closes the door 100). In some embodiments, the control system 96 may be configured to open and/or close the door 100 when the ride vehicle 14 reaches a predetermined position along the ride path 18. Additionally or alternatively, the control system 96 is configured to open and/or close the door 100 upon detecting (e.g., via a load sensor) that the article 12 has been placed in the compartment 16. In other embodiments, the door 100 is opened and/or closed manually by a guest and/or operator of the amusement park ride.

In any case, the door 100 of the first compartment 140 may open (e.g., the control system 96 controls the actuator 143 that opens and closes the door 100) when a subsequent guest enters the ride vehicle 14 at the loading region, for example. The subsequent guest may then remove the second article 12 from the first compartment 140 and utilize the clean second article 12 throughout the duration of the amusement park ride. Further, the first article 12 is simultaneously sanitized in the second compartment 142 as the subsequent guest uses the second article 12.

In one embodiment, the article 12 must be disposed in the appropriate container to release a ride constraint 144 (e.g., ride restraint) of the ride vehicle 14. For instance, the ride vehicle 14 may include the ride constraint 144 to generally block movement of guests within the ride vehicle 14. At the loading region of the ride path 18, the ride constraint 144 may secure (e.g., lock) into place, such that the guest in the ride vehicle 14 may not substantially move the ride restraint 144 as the ride vehicle 14 travels from the loading region to the unloading region. When the ride vehicle 14 reaches the unloading region, the guest may dispose the article 12 into the first compartment 140 and/or the second compartment 142 depending on which of the compartments 140 or 142 is empty (e.g., the appropriate compartment without the article 12). In some embodiments, the control system 96 detects the article 12 within the appropriate compartment 140 and/or 142 (e.g., via a load sensor) and releases the ride restraint 144 to enable the guest to exit the ride vehicle 14. Further, the control system 96 may close the door 100 of the appropriate compartment 140 and/or 142 via the actuator 143 upon detecting that the article 12 is within the appropriate compartment 140 and/or 142. Further still, the control system 96 may open the door 100 (e.g., via the actuator 143) of the first compartment 140 and/or the second compartment 142 that includes the article 12 that underwent sanitization during the previous ride iteration.

In some embodiments, the ride restraint 144 is coupled to the door 100 of the first compartment 140 and/or the second compartment 142 via a gear system or other physical connection, such that the ride restraint 144 is released simultaneously with the closing and/or opening of the door 100 of the first compartment 140 and/or the second compartment 142. In other embodiments, the ride restraint 144 is released when the door 100 is manually closed. For example, the control system 96 may detect that the door 100 of the appropriate compartment 140 and/or 142 has been closed by the guest and/or an operator, and subsequently release the ride constraint 144. In other embodiments, the physical connection between the ride restraint 144 and the door 100 of the first compartment 140 and/or the second compartment 142 may release the ride restraint 144 as the door 100 of the appropriate compartment 140 and/or 142 closes.

Figure 6:
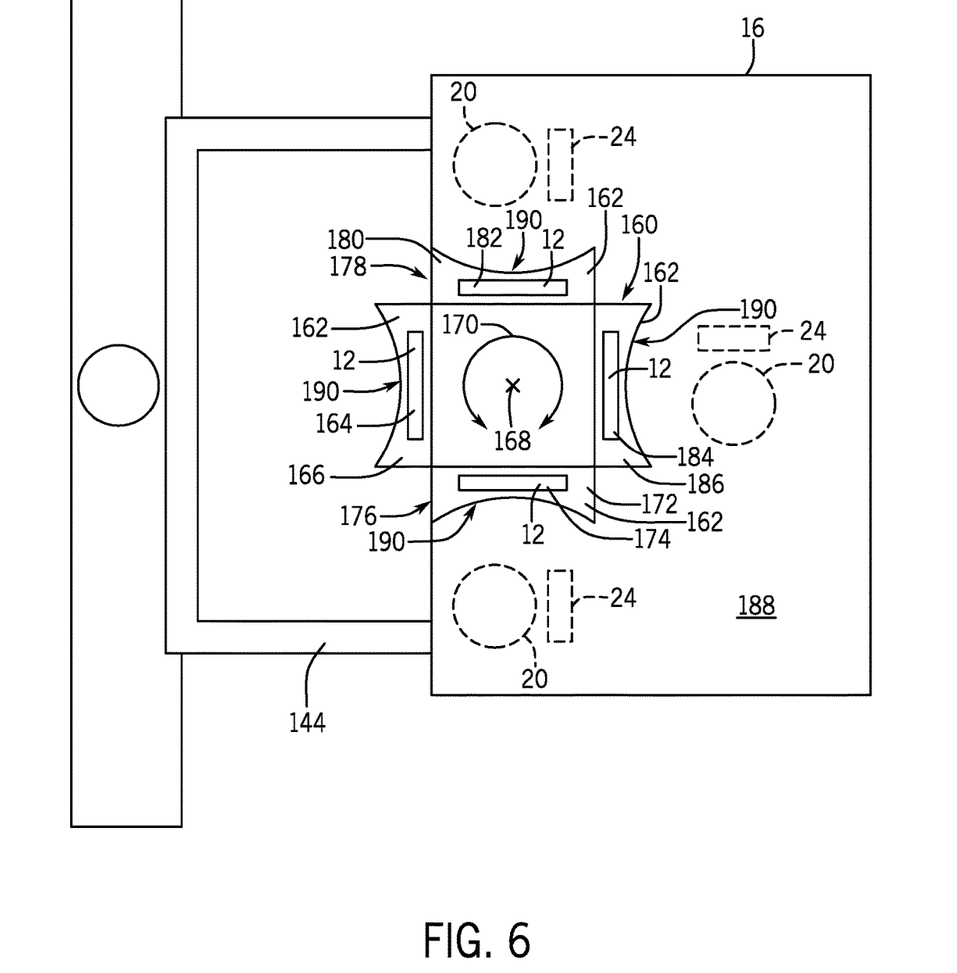
FIG. 6 illustrates an elevation view of an embodiment of an article rotation device for the compartment of the sanitization system, in accordance with an aspect of the present disclosure.

In the illustrated embodiment of FIG. 5, the ride vehicle 14 includes multiple compartments 16, which may consume a relatively large amount of space within the ride vehicle 14. As such, it is now recognized that it may be desirable to include a device that enables rotation between a plurality of articles 12 within a single compartment 16. For example, FIG. 6 illustrates a plan view of an embodiment of the compartment 16 having an article carousel or rotation device 160. As shown in the illustrated embodiment of FIG. 6, the article rotation device 160 includes a plurality of receptacles 162, where each receptacle 162 of the plurality of receptacles 162 is configured to receive and secure an article 12 with respect to the compartment 16. While the illustrated embodiment of FIG. 6 shows the article rotation device 160 having four of the receptacles 162, it should be noted that the article rotation device 160 may include two, three, five, six, seven, eight, nine, ten, or more than ten of the receptacles 162. In some embodiments, engaging or disengaging the ride restraint 144 (e.g., a lap bar) may actuate the article rotation device 160 or a related access door to rotate and/or otherwise open to enable a guest to utilize a sanitized article 12.

In any event, the article rotation device 160 enables a plurality of the articles 12 to alternate between the sanitization process and utilization by guests of the amusement park ride. For instance, a first article 164 (e.g., previously sanitized within the compartment 16) is disposed in a first receptacle 166 that is positioned external to the compartment 16. The guest may remove the clean first article 164 from the first receptacle 166 and utilize the first article 164 throughout the duration of the amusement park ride (e.g., when the ride vehicle 14 travels from the loading region to the unloading region along the ride path 18). At the conclusion of the amusement park ride (e.g., when the ride vehicle 14 reaches the unloading region), the guest may be prompted to place the first article 164 back into the first receptacle 166. The control system 96 may then actuate the article rotation device 160 (e.g., via a motor) to rotate about an axis 168 in a circumferential direction 170. As such, a second receptacle 172 having a second article 174 may be positioned external to the compartment 16, such that a subsequent guest may utilize the clean second article 174.

As shown in the illustrated embodiment of FIG. 6, when the first receptacle 166 is positioned external to the compartment 16, a surface 176 of the second receptacle 172 and a surface 178 of a third receptacle 180 seal the compartment 16. Therefore, the ultraviolet light 22 and the sanitizing mist or spray 26 may be directed toward the second article 174, a third article 182, and/or a fourth article 184 (disposed in a fourth receptacle 186), which are each positioned internal to the compartment 16, without the ultraviolet light 22 and/or the sanitizing mist or spray 26 exiting from an internal portion 188 of the compartment 16. In other words, the surfaces 176 and 178 block the ultraviolet light 22 and/or the sanitizing mist or spray 26 from exiting the compartment 16 and reaching portions of the ride vehicle 14 that include the guests. In other embodiments, at least a portion of the ultraviolet light 22 and/or the sanitizing mist or spray 26 may be configured to exit the compartment 16.

In some embodiments, the compartment 16 includes a plurality of the ultraviolet light sources 20 and a plurality of the nozzles 24 to expose the articles 164, 174, 182, and/or 184 to the ultraviolet light 22 and the sanitizing mist or spray 26, respectively, as the receptacles 166, 172, 180, and/or 186 rotate positions within the compartment 16. For example, the compartment 16 may include a number of ultraviolet light sources 20 and nozzles 24 (e.g., three) that corresponds to a number of the receptacles 166, 172, 180, and/or 186 that are positioned within the compartment 16 at any given time (e.g., three). As such, the articles 164, 174, 182, and/or 184 undergo multiple sanitization processes before the articles 164, 174, 182, and/or 184 are positioned external to the compartment 16 and ultimately utilized by the guests of the amusement park ride. In other embodiments, the compartment 16 may have a smaller number of the ultraviolet light sources 20 and the nozzles 24 than a number of the receptacles 162 on the article rotation device 160 (see, e.g., FIGS. 8 and 9). In still further embodiments, the compartment 16 may include a greater number of the ultraviolet light sources 20 and the nozzles 24 than a number of the receptacles 162 included on the article rotation device 160.

As shown in the illustrated embodiment of FIG. 6, the receptacles 166, 172, 180, and/or 186 may each include a curved surface 190 that is configured to facilitate rotation of the article rotation device 160. In other embodiments, the receptacles 166, 172, 180, and/or 186 include other structural configurations that facilitate rotation of the article rotation device 160 while providing sufficient space to accommodate the respective articles 164, 174, 182, and/or 184 within the receptacles 166, 172, 180, and/or 186.

Figure 7:
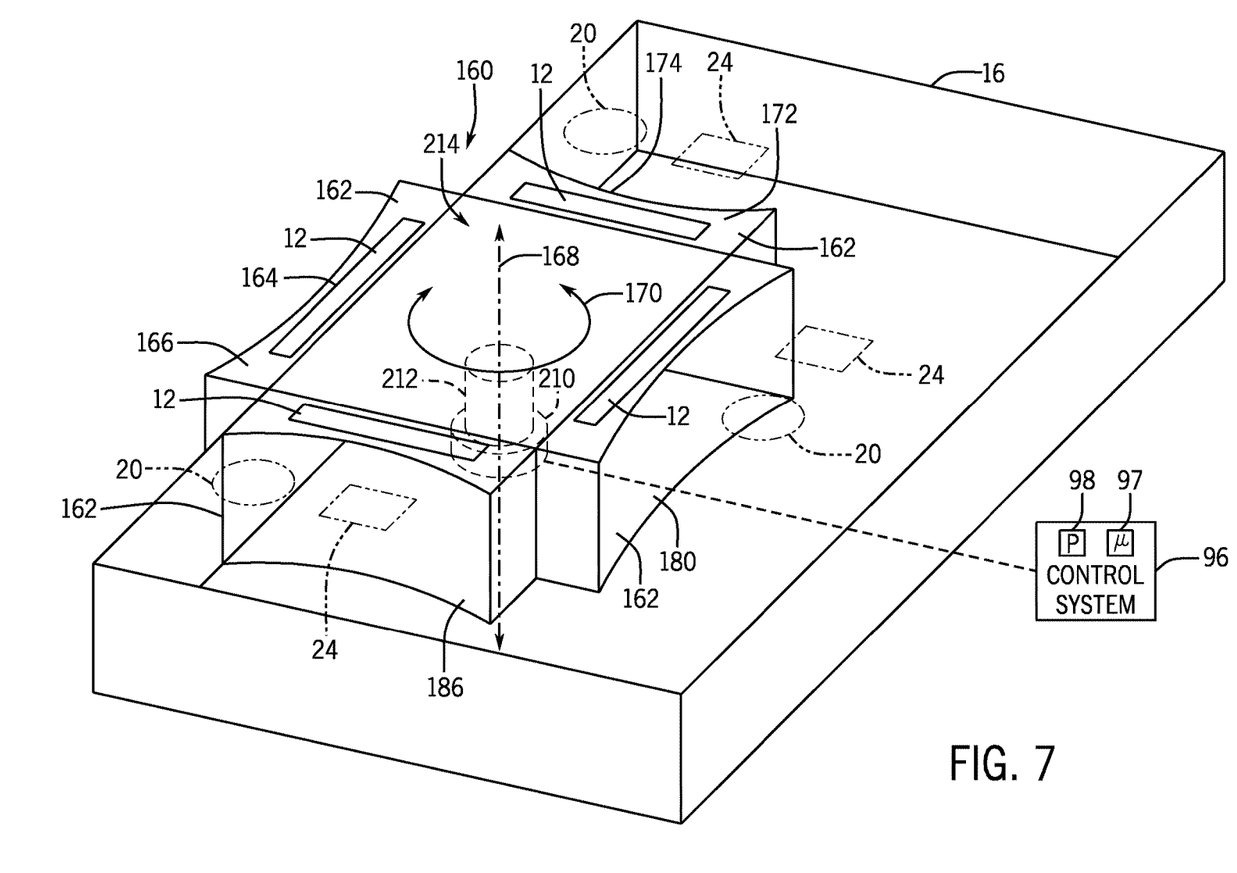
FIG. 7 illustrates a perspective view of an embodiment of the article rotation device of FIG. 6, in accordance with an aspect of the present disclosure.

FIG. 7 is a perspective view of the article rotation device 160 of FIG. 6 illustrating a motor 210 coupled to an actuator 212 that drives rotation of the article rotation device 160. As shown in the illustrated embodiment of FIG. 7, the actuator 212 is coupled to a body 214 of the article rotation device 160. The body 214 is driven about the axis 168 in the circumferential direction 170. Further, each of the receptacles 166, 172, 180, and/or 186 are coupled to the body 214 via fasteners, an adhesive, welding, or another suitable technique. In other embodiments, the receptacles 166, 172, 180, and/or 186 are integral with (e.g., formed from a single, or common, piece of material) the body 214. In any case, rotation of the body 214 driven by the motor 210 causes rotation of the receptacles 166, 172, 180, and/or 186.

In some embodiments, the motor 210 is communicatively coupled to the control system 96, such that the control system 96 controls rotation of the article rotation device 160. As discussed above, the control system 96 may receive feedback indicative of a position of the ride vehicle 14 along the ride path 18. As such, the control system 96 may be configured to actuate rotation of the article rotation device 160 based on a position of the ride vehicle 14. For example, when the control system 96 determines that the ride vehicle 14 is at the unloading region and/or between the unloading region and the loading region (e.g., a portion of the ride path 18 where guests are not present on the ride vehicle 14), the control system 96 may actuate the motor 210 to rotate the article rotation device 160 approximately (e.g., within 10% of, within 5% of, or within 1% of) a quarter-turn. As such, the first article 164 disposed in the first receptacle 166 becomes positioned within the compartment 16, where the first article 164 is sanitized during the next iteration of the amusement park ride. Similarly, the second article 174 within the second receptacle 172 is positioned external to the compartment 16. As such, a guest may remove the second article 174 from the second receptacle 172 for use during the next iteration of the amusement park ride. As used herein, an iteration of the amusement park ride refers to the ride vehicle 14 traveling from the loading region of the ride path 18, to the unloading region of the ride path 18, and back to the loading region of the ride path 18 (e.g., a single completion of traveling a full length of the ride path 18 in the direction of the ride vehicle 14).

Accordingly, the article rotation device 160 of FIGS. 6 and 7 enables four of the articles 12 to rotate between guest uses as the ride vehicle 14 travels along the ride path 18. In other words, three of the four articles 12 are sanitized, while one of the four articles 12 is utilized by the guest in the ride vehicle 14 experiencing the amusement park ride. Therefore, the articles 12 may not be required to be removed from the ride vehicle 14 to undergo sanitization, thereby reducing a time for sanitizing the articles 12 and/or reducing a number of the articles 12 purchased and/or made available by the amusement park. As such, more guests of the amusement park may experience the amusement park ride over a given operating time and capital costs of the amusement park may be reduced.

Figure 8:
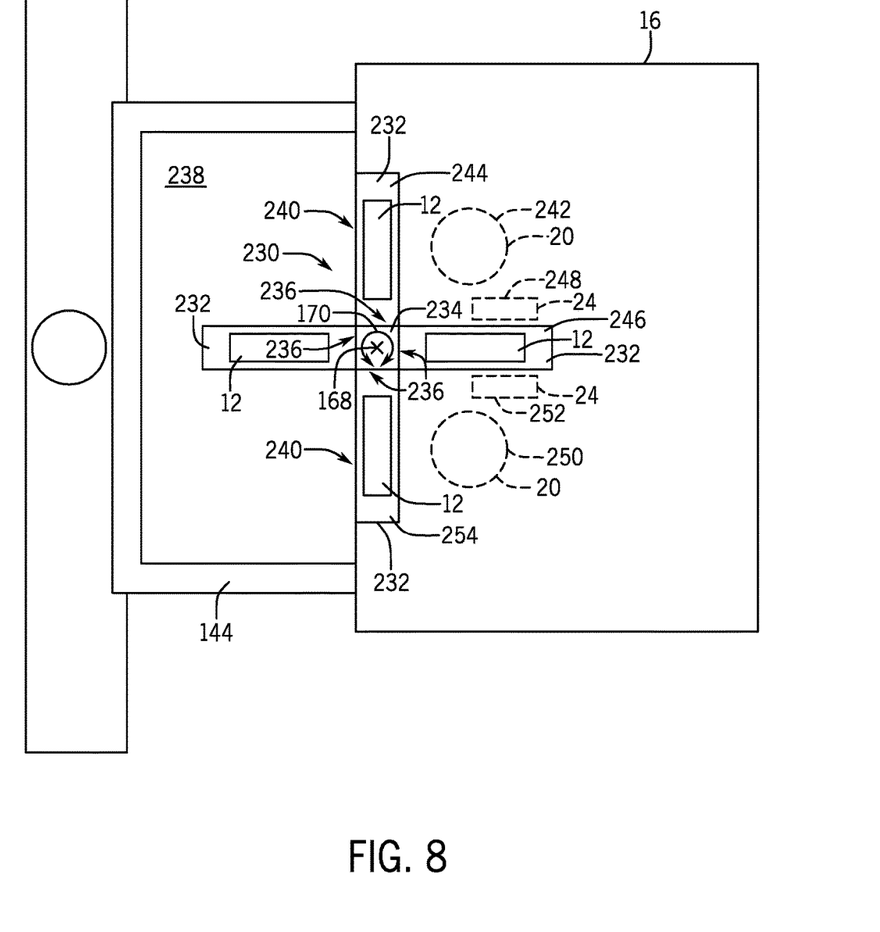
FIG. 8 illustrates an elevation view of an embodiment of an article rotation device for the compartment of the sanitization system, in accordance with an aspect of the present disclosure.

FIG. 8 is a plan view of an embodiment of an article rotation device 230 disposed at least partially in the compartment 16. As shown in the illustrated embodiment of FIG. 8, the article rotation device 230 includes a plurality of receptacles 232 disposed about a body 234 of the article rotation device 230. The body 234 of the article rotation device 230 may include a reduced size when compared to the body 214 of the article rotation device 160 because a smaller surface 236 of the plurality of receptacles 232 abuts outer surfaces of the body 234. However, the plurality of receptacles 232 may extend further into a space 238 of the ride vehicle 14. In other embodiments, the plurality of receptacles 232 include a different shape (e.g., pyramidal, spherical, or polygonal) such that other sizes and/or configurations of the body 234 may be utilized. As discussed above, surfaces 240 of the plurality of receptacles 232 form a seal of the compartment 16, such that the sanitization process may occur as the ride vehicle 14 travels along the ride path 18.

The compartment 16 includes one or more of the ultraviolet light sources 20 and one or more of the nozzles 24. In some embodiments, the one or more ultraviolet light sources 20 and the one or more nozzles 24 are shared between adjacent receptacles 232 of the plurality of receptacles 232. For instance, a first ultraviolet source 242 is shared between a first receptacle 244 and a second receptacle 246, adjacent to the first receptacle 244. Similarly, a first nozzle 248 is shared between the first receptacle 244 and the second receptacle 246. Further, a second ultraviolet source 250 and/or a second nozzle 252 may be shared between the second receptacle 246 and a third receptacle 254. In some embodiments, each receptacle 232 of the plurality of receptacles 232 is disposed within the compartment 16 for multiple iterations (e.g., three) of the amusement park ride before a guest utilizes a corresponding article 12 disposed in a respective receptacle 232. Therefore, the compartment 16 may be configured to provide slightly less exposure to the ultraviolet light 22 and/or the sanitizing spray or mist 26 to each receptacle 232 when compared to embodiments where the corresponding article 12 is utilized every other iteration of the amusement park ride.

Figure 9:
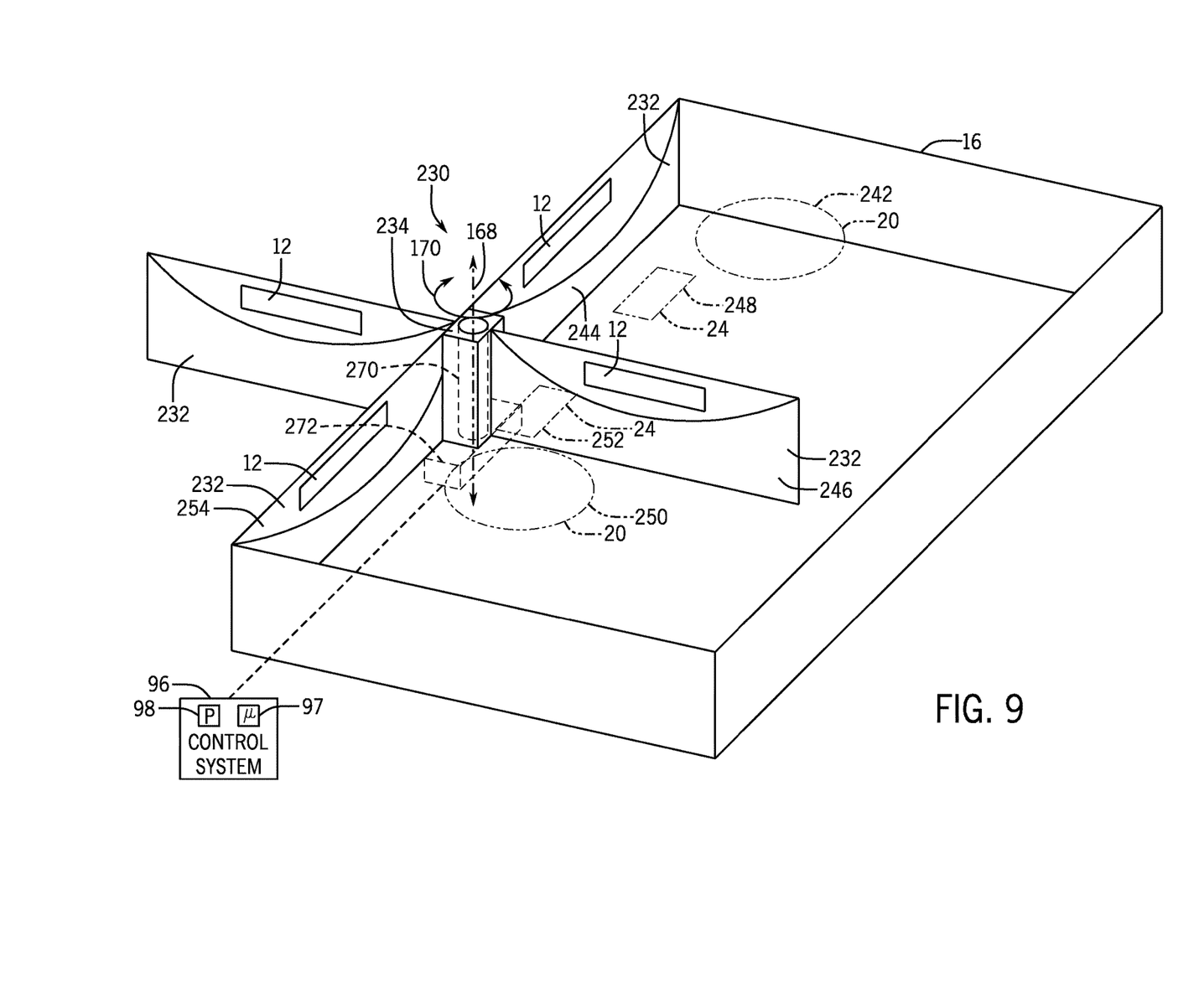
FIG. 9 illustrates a perspective view of an embodiment of the article rotation device of FIG. 8, in accordance with an aspect of the present disclosure.

FIG. 9 illustrates a perspective view of the article rotation device 230, where an actuator 270 is driven by a motor 272 to rotate the article rotation device 230. As shown in the illustrated embodiment of FIG. 9, the actuator 270 is coupled to the body 234 of the article rotation device 230. The body 234 is driven about the axis 168 in the circumferential direction 170. In some embodiments, the motor 272 is communicatively coupled to the control system 96, such that the control system 96 controls rotation of the article rotation device 230. As discussed above, the control system 96 may receive feedback indicative of a position of the ride vehicle 14 along the ride path 18. As such, the control system 96 may be configured to actuate rotation of the article rotation device 230 based on a position of the ride vehicle 14. For example, when the control system 96 determines that the ride vehicle 14 is at the unloading region and/or between the unloading region and the loading region (e.g., a portion of the ride path 18 where guests are not present on the ride vehicle 14), the control system 96 may actuate the motor 272 to rotate the article rotation device 230 approximately (e.g., within 10% of, within 5% of, or within 1% of) a quarter-turn. In other embodiments, the control system 96 may actuate the motor 272 to rotate the article rotation device 230 another suitable amount. For instance, the amount of rotation of the article rotation device 230 may depend on a number of the receptacles 232 of the plurality of receptacles 232 and/or a spacing of the plurality of receptacles 232 around the body 234. In any case, at least one receptacle 232 of the plurality of receptacles 232 may be external to the compartment 16 to enable a guest to remove the article 12 from the at least one receptacle 232 and utilize the article 12 throughout a duration of the amusement park ride (e.g., one iteration), while at least one other receptacle 232 of the plurality of receptacles 232 is disposed within the compartment 16 and undergoes the sanitization process. In some embodiments, actuation of the ride restraint 144 may depend on a position of the article rotation device 230. For instance, the rotation of the article rotation device 230 driven by the motor 272 may cause the ride restraint 144 to release and enable guests to exit the ride vehicle 14. In other embodiments, release of the ride restraint 144 may cause actuation of the motor 272 to drive rotation of the article rotation device 230.

While only certain features of the disclosure have been illustrated and described herein, many modifications and changes will occur to those skilled in the art. It is, therefore, to be understood that the appended claims are intended to cover all such modifications and changes as fall within the true spirit of the present disclosure. The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

The invention claimed is:

1. A sanitization system for an amusement park, comprising:
    a compartment disposed in a ride vehicle of an amusement park ride, wherein the compartment is configured to receive an article of the amusement park ride;
    an ultraviolet light source disposed in the compartment, wherein the ultraviolet light source is configured to transmit ultraviolet light toward a surface of the article when the article is positioned in the compartment; and
    a nozzle disposed in the compartment, wherein the nozzle is configured to direct a sanitizing fluid toward the surface of the article when the article is positioned in the compartment.

2. The system of claim 1, comprising a control system configured to detect a position of the ride vehicle along a ride path of the amusement park ride, wherein the control system is configured to activate the ultraviolet light source, the nozzle, or both, when the control system determines that the ride vehicle is positioned at a particular position along the ride path.

3. The system of claim 2, wherein the compartment comprises a door configured to seal the compartment when the ultraviolet light source, the nozzle, or both are activated, and wherein the control system is configured to actuate the door based on a sensed location of the ride vehicle along the ride path.

4. The system of claim 1, wherein the sanitization system comprises an article rotation device at least partially disposed in the compartment, wherein the article rotation device comprises a plurality of receptacles, and wherein each receptacle of the plurality of receptacles is configured to receive a corresponding article of the amusement park ride.

5. The system of claim 4, wherein the plurality of receptacles is coupled to a body of the article rotation device, wherein an actuator is coupled to the body, and wherein the actuator is configured to rotate the body and the plurality of receptacles.

6. The system of claim 5, wherein a motor is coupled to the actuator and is configured to drive rotation of the actuator, wherein a control system is communicatively coupled to the motor, and wherein the control system is configured to control operation of the motor based at least on a position of the ride vehicle along a ride path of the amusement park ride.

7. The system of claim 1, wherein the sanitization system comprises a rack disposed in the compartment, and wherein the rack is configured to position the article of the amusement park ride, such that the surface of the article is exposed to the ultraviolet light and the sanitizing fluid when the article is positioned in the compartment.

8. The system of claim 7, wherein the rack comprises a pair of protrusions extending from a bottom surface of the compartment.

9. The system of claim 1, wherein the compartment comprises a drain configured to direct residual sanitizing fluid toward a storage tank, a waste container, or both.

10. The system of claim 9, wherein the sanitization system comprises a pump configured to direct the sanitizing fluid from the storage tank to the nozzle, direct the sanitizing fluid from the drain to the storage tank, direct the sanitizing fluid from the drain to the waste container, or any combination thereof.

11. The system of claim 1, wherein the sanitization system comprises a fan, dryer, or heater configured to remove residual sanitizing fluid from the surface of the article of the amusement park ride.

12. The system of claim 1, wherein the article of the amusement park ride comprises a pair of glasses for viewing 3-dimensional videos, clips, or effects, virtual reality goggles, augmented reality goggles, or a combination thereof.

13. A system, comprising:
an amusement park ride, comprising a ride path and a ride vehicle, wherein the ride vehicle is configured to transport a guest along the ride path in a direction of the amusement park ride; and
a sanitization system of the amusement park, wherein the sanitization system is disposed within the ride vehicle, and wherein the sanitization system comprises:
a compartment configured to receive an article of the amusement park ride;
an ultraviolet light source disposed in the compartment, wherein the ultraviolet light source is configured to transmit ultraviolet light toward a surface of the article when the article is positioned in the compartment; and
a nozzle disposed in the compartment, wherein the nozzle is configured to direct a sanitizing fluid toward the surface of the article when the article is positioned in the compartment.

14. The system of claim 13, wherein the ride path comprises an unloading region for the guest to exit the ride vehicle and a loading region for the guest to enter the ride vehicle.

15. The system of claim 14, comprising a control system communicatively coupled to the ultraviolet light source and a flow control device of the sanitizing fluid, wherein the control system is configured to receive feedback indicative of a position of the ride vehicle along the ride path, and wherein the control system is configured to activate the ultraviolet light source, the flow control device of the sanitizing fluid, or both, when the ride vehicle is determined to be traveling from the unloading region to the loading region of the ride path.

16. The system of claim 13, comprising a second compartment configured to receive a second article of the amusement park ride, and wherein the second compartment comprises a second ultraviolet light source, a second nozzle, or both.

17. A system, comprising:
a sanitization system of an amusement park, wherein the sanitization system is disposed within a ride vehicle of an amusement park ride, and wherein the sanitization system comprises:
a compartment configured to receive an article of the amusement park ride;
an ultraviolet light source disposed in the compartment, wherein the ultraviolet light source is configured to transmit ultraviolet light toward a surface of the article when the article is positioned in the compartment; and
an article rotation device at least partially disposed in the compartment, wherein the article rotation device comprises a plurality of receptacles, and wherein each receptacle of the plurality of receptacles is configured to receive a corresponding article of the amusement park ride.

18. The system of claim 17, wherein the plurality of receptacles is coupled to a body of the article rotation device, wherein an actuator is coupled to the body, and wherein the actuator is configured to rotate the body and the plurality of receptacles.

19. The system of claim 18, comprising a control system configured to rotate the actuator a fraction of a turn after each iteration of the amusement park ride.

20. The system of claim 19, wherein rotation of the article rotation device is configured to release a ride restraint of the ride vehicle.

* * * * *